US008933248B2

(12) United States Patent
Rao et al.

(10) Patent No.: US 8,933,248 B2
(45) Date of Patent: Jan. 13, 2015

(54) 3-SUBSTITUTED-3-HYDROXY OXINDOLE DERIVATIVES AND PROCESS FOR PREPARATION THEREOF

(71) Applicant: Council of Scientific & Industrial Research, New Delhi (IN)

(72) Inventors: Mandapati Mohan Rao, Hyderabad (IN); Parvathaneni Sai Prathima, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/921,957

(22) Filed: Jun. 19, 2013

(65) Prior Publication Data

US 2013/0345438 A1   Dec. 26, 2013

(30) Foreign Application Priority Data

Jun. 21, 2012   (IN) .......................... 1914/DEL/2012
Apr. 2, 2013    (IN) .......................... 1914/DEL/2012

(51) Int. Cl.
C07D 209/38   (2006.01)

(52) U.S. Cl.
CPC .................................. C07D 209/38 (2013.01)
USPC ....................................................... 548/485

(58) Field of Classification Search
CPC ..................................................... C07D 209/38
USPC ....................................................... 548/485
See application file for complete search history.

(56) References Cited

U.S. PATENT DOCUMENTS

| 5,047,554 | A | 9/1991 | Ehrgott et al. |
| 7,595,338 | B2 | 9/2009 | Wilk |
| 2004/0014986 | A1 | 1/2004 | Hendel et al. |
| 2011/0105804 | A1 | 5/2011 | Major et al. |

OTHER PUBLICATIONS

Chafeev, et al. Document No. 145:454931, retrieved from CAPLUS, Oct. 27, 2006.*

* cited by examiner

Primary Examiner — Shawquia Jackson
(74) Attorney, Agent, or Firm — Maschoff Brennan

(57) ABSTRACT

The present invention relates to expedient method for synthesis of 3-substituted-3-hydroxy-oxindole derivatives, which are useful as synthetic precursors to valuable pharmaceutical compounds. These are synthesized by reacting nitromethane with the corresponding isatins of formula (I). The reaction process of isatins was carried using water as a solvent at room temperature to form the corresponding 3-hydroxy-3-nitromethylindolin-2-ones of formula (II).

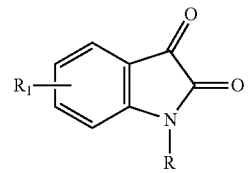

(I)

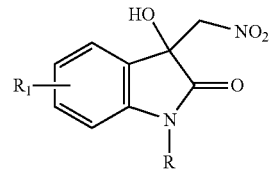

(II)

10 Claims, No Drawings

3-SUBSTITUTED-3-HYDROXY OXINDOLE DERIVATIVES AND PROCESS FOR PREPARATION THEREOF

FIELD OF THE INVENTION

The present invention relates to novel 3-substituted-3-hydroxy oxindole derivatives. Particularly, the present invention relates to novel 3-hydroxy-3-nitromethylindolin-2-one derivatives. The present invention also relates to simple and convenient process for the preparation of 3-substituted-3-hydroxy-oxindole derivatives and more particularly, to simple and convenient process for the preparation of 3-hydroxy-3-nitromethylindolin-2-one and its derivatives.

BACKGROUND OF THE INVENTION

Oxindoles, with C-3 functionalisation resulting in quaternary centre at C-3 position constitute a common structural backbone for several drug candidates and bioactive natural products. In particular, 3-substituted-3-hydroxyoxindole is an emerging scaffold for several pharmacologically active alkaloids such as dioxibrassinine, CPC-1, Donaxaridine, Maremycin A and B, Horsfiline, spirobrassinin in addition to several others contain 3-hydroxyoxindole moiety.

For detailed discussion of biological significance of 3-substituted-3-hydroxyoxindoles refer "3-Substituted-3-hydroxy-2-oxindole, an Emerging New Scaffold for Drug Discovery with Potential Anti-Cancer and other Biological Activities" reported by Peddibhotla in *Curr. Bioact. Compd.* 2009, 5, 20. In this review paper synthesis, isolation, bioactivity and medicinal chemistry aspects of these 3-substituted-3-hydroxyoxindoles scaffolds are described.

It is important to note that, prior to 1935, 3-hydroxy-3-nitromethylindolin-2-ones (which is a Henry Adduct) had never been successfully prepared. In 1936 the synthesis of 3-hydroxy-3-nitromethylindolin-2-ones was achieved for the first time [Lindwall J. Am. Chem. Soc. 58, 1236 (1936)]. The inherent disadvantages of the process adopted by Lindwall are the usage of additives and expensive solvents with low yields of the desired products in long reaction hours.

Reference may be made to the publication, Tetrahedron 2008, 64, 5915 wherein synthesis of 3-hydroxy-3-nitromethylindolin-2-ones was achieved by electro-catalytic methods. The inherent disadvantages of the disclosed process are the usage of expensive solvents with low yields of the desired products.

Reference may be made to the publication, Tetrahedron Letters 2011, 52, 5862 wherein synthesis of 3-hydroxy-3-nitromethylindolin-2-ones was attained using DABCO as catalyst. The inherent disadvantage of the disclosed process is the usage of expensive DABCO ligand and difficulty in the recovery of pure product as under strong basic conditions there is every possibility of rearrangement of the product.

Other related prior arts on oxindoles are:

| | | |
|---|---|---|
| US 2004/0014986 A1 | January 2004 | Hendel et al |
| U.S. Pat. No. 7,595,338 B2 | September 2009 | Wilk et al |
| U.S. Pat. No. 5,047,554 B2 | September 1991 | Ehrgott et al |
| US 2011/0105804 A1 | May 2011 | Major et al |

Despite the continued interest being shown, there is a continued need to develop further derivatives of 3-hydroxy-3-nitromethylindolin-2-ones and also to develop efficient and less expensive synthetic route for preparing 3-hydroxy-3-nitromethylindolin-2-one and its further derivatives which can be used as value added synthetic precursors, wherein such value added synthetic precursors can act as starting materials for several useful drug candidates.

OBJECTS OF THE INVENTION

The main object of the present invention is to provide novel 3-hydroxy-3-nitromethylindolin-2-one derivatives which act as value added synthetic precursors and as starting materials for several useful drug candidates.

Another object of the invention is to provide a green catalytic, cheap, safe and environmentally benign method for preparing 3-hydroxy-3-nitromethylindolin-2-one and its further derivatives in high yields.

SUMMARY OF THE INVENTION

The present invention pertains to novel 3-hydroxy-3-nitromethylindolin-2-one derivatives. The so obtained novel derivatives, which are basically Henry adducts and which are value added synthetic precursors which can act as starting materials for several useful drug candidates, especially anti-cancer compounds. The so obtained novel derivatives are valuable synthetic intermediates for several organic transformations especially in the synthesis of 1,2 amino alcohols.

Accordingly the present invention provides novel compounds of general formula II:

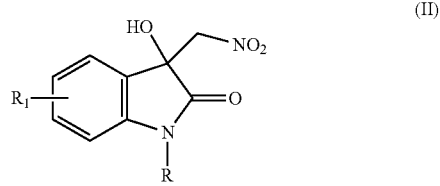

wherein:
R=H or $C_7H_6$—X;
$R_1$=H, $X_1$ at C-7 position, or $X_2$ at C-5 position;
X=H, Br, or Cl;
$X_1$=I or F;
$X_2$=H, Cl or Br,
wherein:
when, R=H; $R_1$=$X_1$ at C-7 position;
when, R=$C_7H_6$—X; then $R_1$=$X_2$ at C-5 position;
when X=H; then $R_1$=Cl at C-5 position;
when X=Cl; then $R_1$=$X_2$ at C-5 position;
when X=Br; then $R_1$=H or Cl at C-5 position;
and
further wherein when $R_1$=H, X is Br at ortho position; and wherein when $R_1$=Cl at C-5 position, X is Br at para position.

In an embodiment of the present invention, the novel 3-hydroxy-3-nitromethylindolin-2-one derivatives include:
  3-hydroxy-7-iodo-3-(nitromethyl)indolin-2-one (represented by STR1);
  7-fluoro-3-hydroxy-3-(nitromethyl)indolin-2-one (represented by STR2);
  1-benzyl-5-chloro-3-hydroxy-3-(nitromethyl)indolin-2-one (represented by STR3);
  1-(2-bromobenzyl)-3-hydroxy-3-(nitromethyl)indolin-2-one (represented by STR4);
  1-(2-chlorobenzyl)-3-hydroxy-3-(nitromethyl)indolin-2-one (represented by STR5);
  1-(4-bromobenzyl)-5-chloro-3-hydroxy-3-(nitromethyl) indolin-2-one (represented by STR6);

5-bromo-1-(2-chlorobenzyl)-3-hydroxy-3-(nitromethyl) indolin-2-one (represented by STR7); and 5-chloro-1-(2-chlorobenzyl)-3-hydroxy-3-(nitromethyl) indolin-2-one (represented by STR8).

In an embodiment of the present invention, the novel 3-hydroxy-3-nitromethylindolin-2-one derivatives have the structure:

STR1
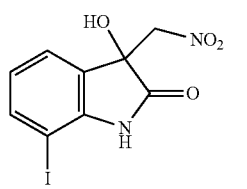

STR2
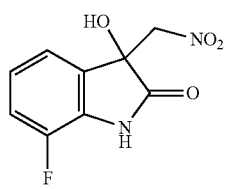

STR3
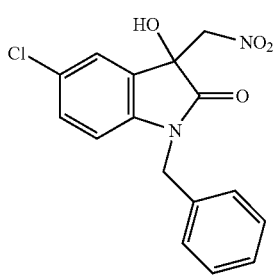

STR4
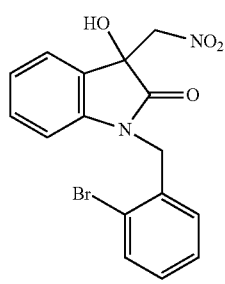

STR5
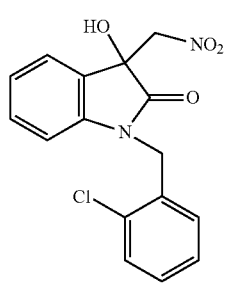

STR6
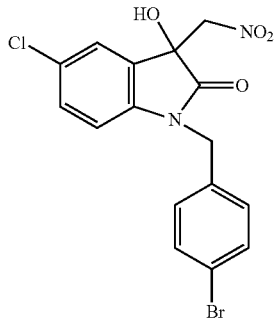

STR7
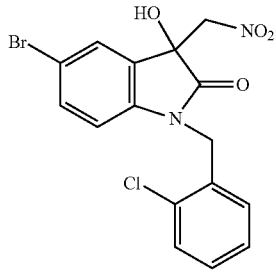

STR8
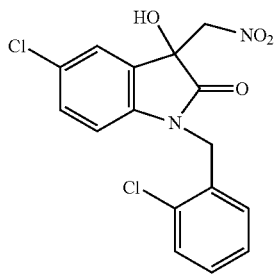

The present invention relates to an improved, convenient, commercially viable, environmentally friendly, cost-effective process for the preparation of 3-hydroxy-3-nitromethylindolin-2-one and its further derivatives using nitromethane and isatin or substituted isatins as starting materials. More particularly, the process provides synthesis of 3-hydroxy-3-nitromethylindolin-2-one and its further derivatives using by reacting nitromethane with isatin or substituted isatins in presence of water as a solvent at about room temperature.

Accordingly the present invention also provides a process for the preparation of 3-hydroxy-3-nitromethylindolin-2-ones of general formula (II):

(II)
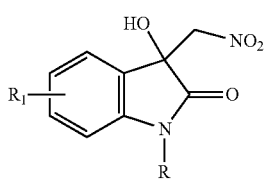

wherein:
R=H; $CH_3$, $C_3H_5$, $C_7H_6$—X;
$R_1$=H, $X_1$ at C-7 position, or $X_2$ at C-5 position;
X=H, Br, or Cl;
$X_1$=F, Cl, Br, or I; and
$X_2$=H, F, Cl, Br, I, $NO_2$, $CH_3$, $OCF_3$;

wherein:
when R=H, then $R_1=X_1$ at C-7 position, or $X_2$ at C-5 position;
when R=$CH_3$, $C_3H_5$, $C_7H_6$—X; then $R_1$=H;
when, R=$C_7H_6$—X; then $R_1=X_2$ at C-5 position;
when X=H, Cl, or Br; then $R_1$=Cl at C-5 position;
when X=Cl; then $R_1$=Br at C-5 position;
comprising the steps:
(a) reacting isatin or a substituted isatin of the formula (I) wherein R and R1 are as described above with nitromethane in aqueous solvent at a temperature ranging between 30 to 50° C. for a period ranging between 10 min to 48 hrs; and

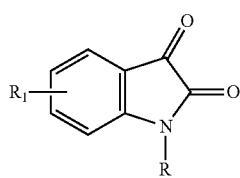

(b) purifying the product by recrystallization or chromatographic methods.

Accordingly the present invention provides a process for the preparation of 3-hydroxy-3-nitromethylindolin-2-ones of general formula (II) comprising:
(a) reacting isatin or a substituted isatin of the formula (I) with nitromethane in aqueous solvent as shown in the below equation at a temperature ranging between 30 to 50° C. for a period ranging between 10 min to 48 hrs; and

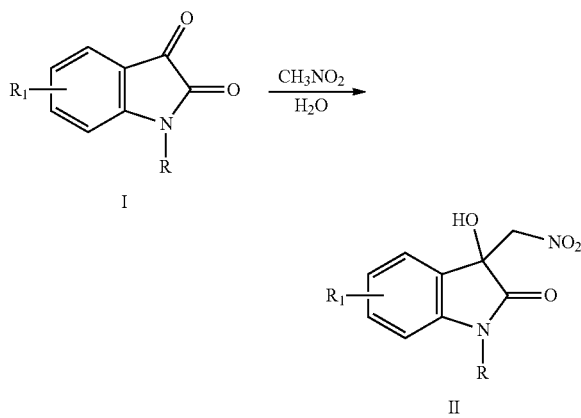

wherein R and R1 in formula I and formula II are:
R=H; $CH_3$, $C_3H_5$, $C_7H_6$—X;
$R_1$=H, $X_1$ at C-7 position, or $X_2$ at C-5 position;
X=H, Br, or Cl;
$X_1$=F, Cl, Br, or I; and
$X_2$=H, F, Cl, Br, I, $NO_2$, $CH_3$, $OCF_3$;
wherein:
when R=H, then $R_1=X_1$ at C-7 position, or $X_2$ at C-5 position;
when R=$CH_3$, $C_3H_5$, $C_7H_6$—X; then $R_1$=H;
when, R=$C_7H_6$—X; then $R_1=X_2$ at C-5 position;
when X=H, Cl, or Br; then $R_1$=Cl at C-5 position;
when X=Cl; then $R_1$=Br at C-5 position; and
(b) purifying the product by recrystallization or chromatographic methods.

In an embodiment of the present invention, the 3-hydroxy-3-nitromethylindolin-2-ones obtained by the process include:
3-hydroxy-3-(nitromethyl)indolin-2-one (represented by STR9);
5-chloro-3-hydroxy-3-(nitromethyl)indolin-2-one (represented by STR10);
5-bromo-3-hydroxy-3-(nitromethyl)indolin-2-one (represented by STR11);
3-hydroxy-5-iodo-3-(nitromethyl)indolin-2-one (represented by STR12);
5-fluoro-3-hydroxy-3-(nitromethyl)indolin-2-one (represented by STR13);
7-chloro-3-hydroxy-3-(nitromethyl)indolin-2-one (represented by STR14);
7-bromo-3-hydroxy-3-(nitromethyl)indolin-2-one (represented by STR15);
3-hydroxy-7-iodo-3-(nitromethyl)indolin-2-one (represented by STR1);
7-fluoro-3-hydroxy-3-(nitromethyl)indolin-2-one (represented by STR2);
3-hydroxy-5-nitro-3-(nitromethyl)indolin-2-one (represented by STR16);
3-hydroxy-5-methyl-3-(nitromethyl)indolin-2-one (represented by STR17);
3-hydroxy-5-trifluoromethoxy-3-(nitromethyl)indolin-2-one (represented by STR18);
3-hydroxy-1-methyl-3-(nitromethyl)indolin-2-one (represented by STR19);
1-benzyl-3-hydroxy-3-(nitromethyl)indolin-2-one (represented by STR20);
1-benzyl-5-chloro-3-hydroxy-3-(nitromethyl)indolin-2-one (represented by STR3);
1-allyl-3-hydroxy-3-(nitromethyl)indolin-2-one (represented by STR21);
1-(2-bromobenzyl)-3-hydroxy-3-(nitromethyl)indolin-2-one (represented by STR4);
1-(2-chlorobenzyl)-3-hydroxy-3-(nitromethyl)indolin-2-one (represented by STR5);
1-(4-bromobenzyl)-5-chloro-3-hydroxy-3-(nitromethyl)indolin-2-one (represented by STR6);
5-bromo-1-(2-chlorobenzyl)-3-hydroxy-3-(nitromethyl)indolin-2-one (represented by STR7); and
5-chloro-1-(2-chlorobenzyl)-3-hydroxy-3-(nitromethyl)indolin-2-one (represented by STR8).

In an embodiment of the present invention, the 3-hydroxy-3-nitromethylindolin-2-ones obtained by the process have the structure:

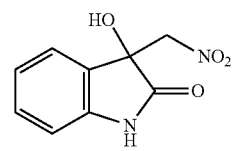

STR9

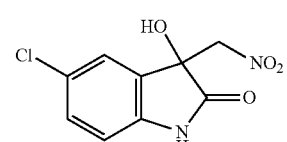

STR10

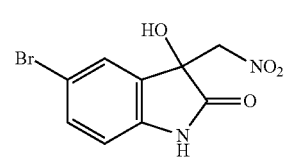

STR11

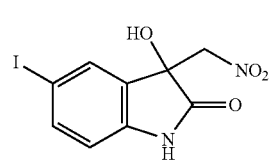 STR12
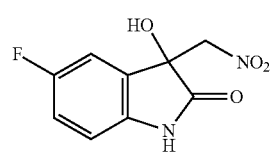 STR13
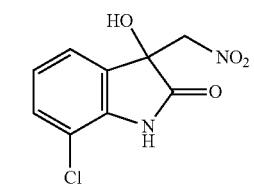 STR14
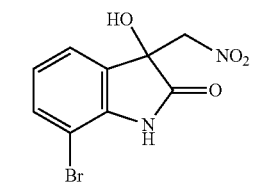 STR15
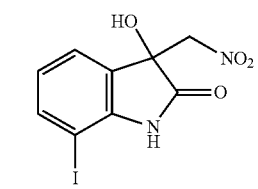 STR1
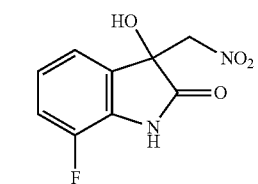 STR2
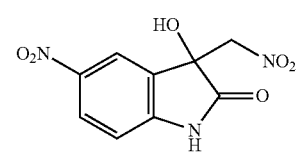 STR16
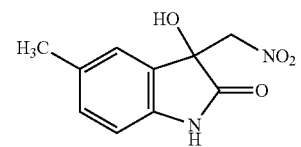 STR17
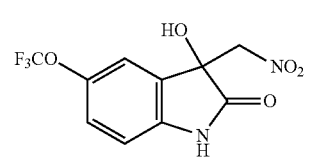 STR18
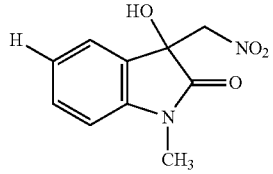 STR19
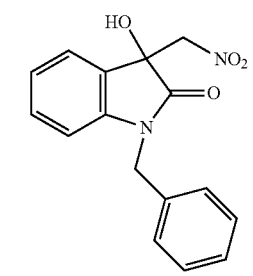 STR20
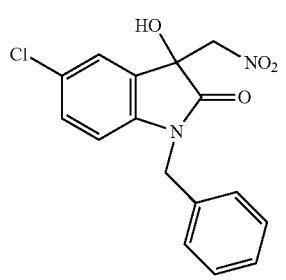 STR3
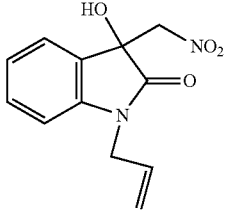 STR20
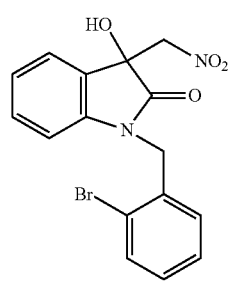 STR4
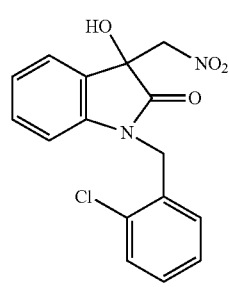 STR5

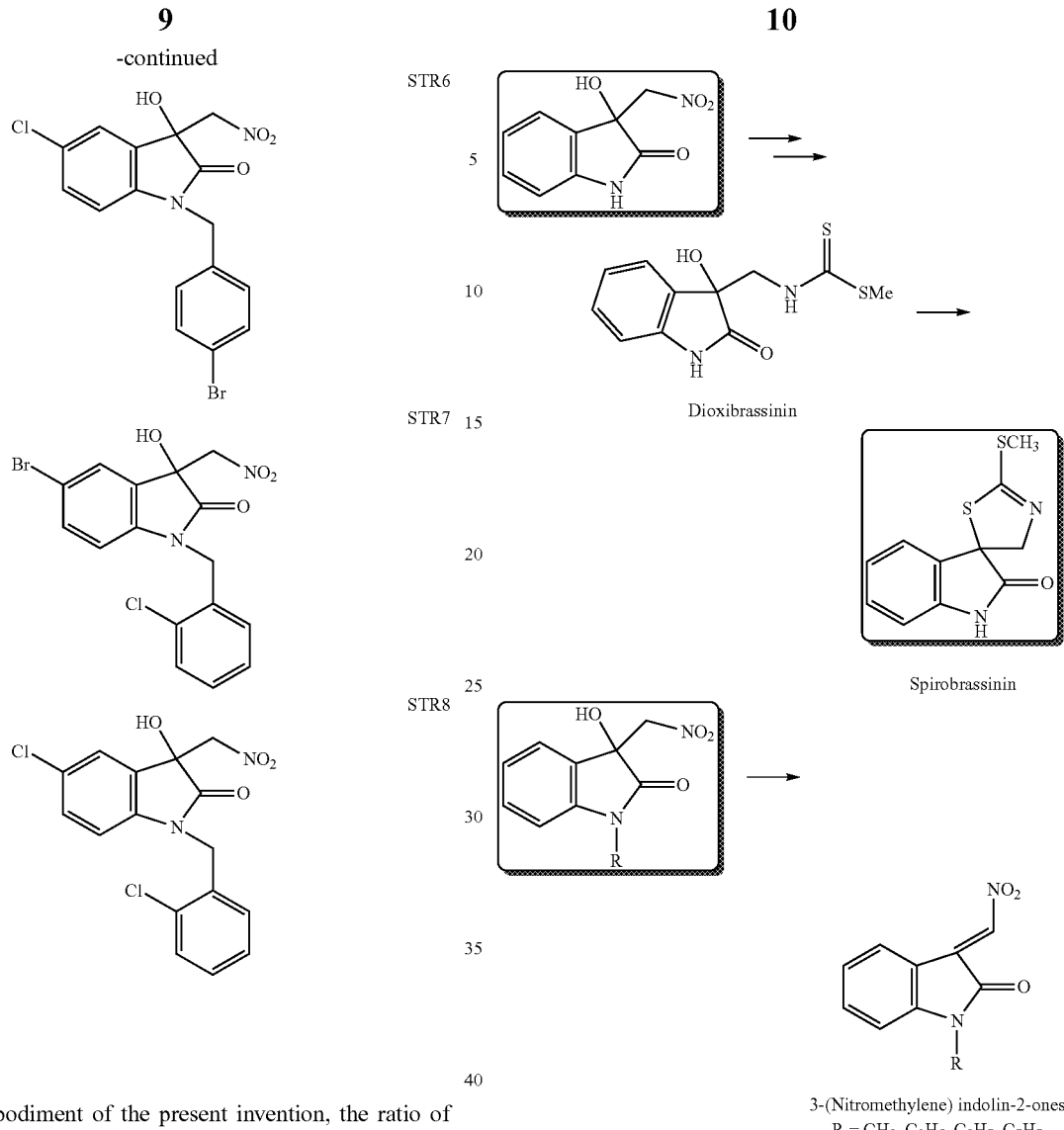

In an embodiment of the present invention, the ratio of isatin or substituted isatin and nitromethane is ranging between 1:3 to 1:5.

In another embodiment of the present invention, the chromatographic method used may be selected from a group consisting of column chromatograph, TLC.

In yet another embodiment of the present invention, the recrystallisation may be carried out using solvent selected from a group consisting of MeOH, EtOAc.

DETAILED DESCRIPTION OF THE INVENTION

The present invention pertains to improved and novel method of preparing oxindole derivatives having substituents attached in the 3-position. The so obtained nitroalcohols are valuable synthetic intermediates for several organic transformations especially in the synthesis of 1,2 amino alcohols.

The 3-substituted-3-hydroxy oxindole derivatives provided in the present invention can be generally termed as Henry adduct and its importance is G. Chen, X. J. Hao, Q. Y. Sun, J. Ding, *Chemical Papers*, 2010, 64, 673-677. By way of a non-limiting example, the 3-substituted-3-hydroxy oxindole derivatives provided in the present invention may be used in the general scheme as shown below:

3-(Nitromethylene) indolin-2-ones
R = $CH_3$, $C_2H_5$, $C_3H_7$, $C_7H_7$

The foregoing and other features of the present invention will be fully understood from the detailed description of illustrative examples. According to certain embodiments, compounds of the invention are represented by general formula as described below.

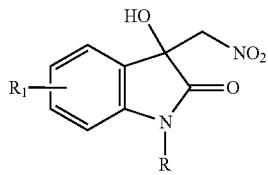
(II)

wherein:
R=H; $CH_3$, $C_3H_5$, $C_7H_6$—X;
$R_1$=H, $X_1$ at C-7 position, or $X_2$ at C-5 position;
X=H, Br, or Cl;
$X_1$=F, Cl, Br, or I; and
$X_2$=H, F, Cl, Br, I, $NO_2$, $CH_3$, $OCF_3$;

wherein:
when R=H, then $R_1=X_1$ at C-7 position, or $X_2$ at C-5 position;
when R=CH$_3$, C$_3$H$_5$, C$_7$H$_6$—X; then $R_1$=H;
when, R=C$_7$H$_6$—X; then $R_1=X_2$ at C-5 position;
when X=H, Cl, or Br; then $R_1$=Cl at C-5 position;
when X=Cl; then $R_1$=Br at C-5 position;

The compounds of this invention are prepared by reacting isatin or substituted isatin of general formula (I) with nitromethane in aqueous medium to give corresponding 3-hydroxy-3-nitromethylindolin-2-ones (II) in high yields according to the following equation.

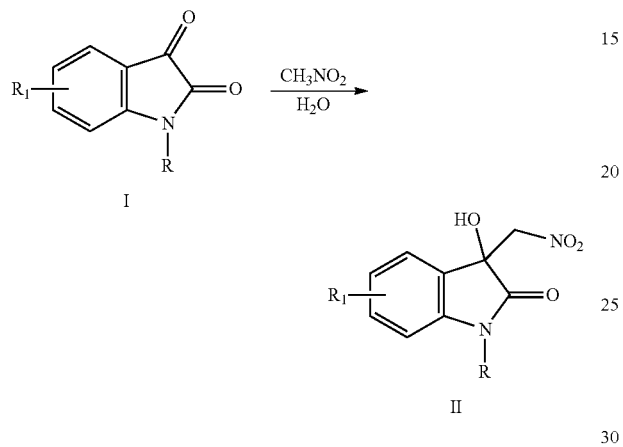

In the following paragraphs, several non-limiting examples to show the working of the claimed invention are demonstrated. It should however, be understood that the scope of the invention is not intended to be restricted to the examples provided below and is intended to be limited only by the appended claims and their equivalents. It may be observed that purely for the ease of illustration and keeping in view the teachings other contained above, in all the following experimental examples described below we have taken the starting materials isatin or substituted isatins and nitromethane in 1:3 molar ratios. It should be however, observed that a person skilled in the art in light of the present disclosure would be in a position to perform the invention in the entire range mentioned in the claims.

For the first time a simple and green method for the synthesis of Henry adducts of various substituted isatin derivatives is described in aqueous medium with several advantages over the existing procedures:
  Water as solvent with no other additives.
  Room temperature reactions.
  Excellent yields.
Following examples are given by way of illustration and should not be construed to limit the scope of the invention.

Example 1

Wherein $R_1$, R=H

Preparation of 3-hydroxy-3-(nitromethyl)indolin-2-one

Isatin (0.073 g) and nitromethane (0.1 ml) were added to water and the reaction mixture was vigorously stirred at a temperature of 30° C. for 10 minutes. The formed solid product was filtered and recrystallized with MeOH to afford pure product.

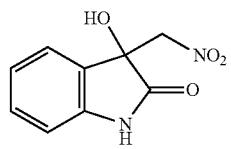

m.p 145° C., HRMS(ESI) for $C_9H_8N_2O_4Na$ [M + Na]$^+$
231.0381 YIELD 98%

Example 2

Wherein, R=H, $R_1$=Cl

Preparation of 5-chloro-3-hydroxy-3-(nitromethyl)indolin-2-one 5-chloroisatin (0.09 g) and nitromethane (0.1 ml) were added to water and the reaction mixture was vigorously stirred at a temperature of 30° C. for 24 hours. The obtained product was extracted with ethyl acetate and purified by silica gel column chromatography using ethyl acetate/hexane as eluents to afford pure product.

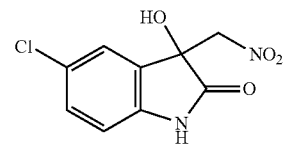

HRMS(ESI) for $C_9H_7N_2O_4ClNa$ [M + Na]$^+$ 264.9992.
YIELD 88%

Example 3

Wherein, R=H, $R_1$=Br

Preparation of 5-bromo-3-hydroxy-3-(nitromethyl)indolin-2-one 5-bromoisatin (0.113 g) and nitromethane (0.15 ml) were added to water and the reaction mixture was vigorously stirred at a temperature of 30° C. for 11 hours. The obtained product was extracted with ethyl acetate and the solvent was removed to give pure product.

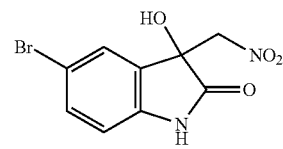

HRMS(ESI) for $C_9H_7N_2O_4BrNa$ [M + Na]$^+$ 308.9486.
YIELD 85%

Example 4

Wherein, R=H, $R_1$=I

Preparation of 3-hydroxy-5-iodo-3-(nitromethyl)indolin-2-one 5-iodoisatin (0.136 g) and nitromethane (0.15 ml) were added to water and the reaction mixture was vigorously stirred at a temperature of 30° C. for 48 hours. The obtained product was extracted with ethyl acetate and purified by silica gel column chromatography using ethyl acetate/hexane as eluents to afford pure product.

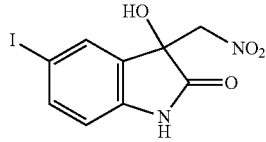

HRMS(ESI) for $C_9H_7N_2O_4INa$ $[M + Na]^+$ 356.9348.
YIELD 90%

Example 5

Wherein, R=H, $R_1$=F

Preparation of 5-fluoro-3-hydroxy-3-(nitromethyl)indolin-2-one 5-fluoroisatin (0.082 g) and nitromethane (0.1 ml) were added to water and the reaction mixture was vigorously stirred at a temperature of 30° C. for 8 hours. The obtained product was extracted with ethyl acetate and purified by silica gel column chromatography using ethyl acetate/hexane as eluents to afford pure product.

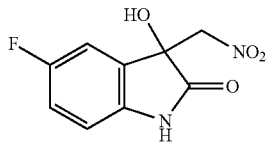

HRMS(ESI) for $C_9H_7N_2O_4FNa$ $[M + Na]^+$ 249.0287.
YIELD 91%

Example 6

Wherein, R=H, $R_1$=Cl

Preparation of 7-chloro-3-hydroxy-3-(nitromethyl)indolin-2-one 7-chloroisatin (0.09 g) and nitromethane (0.1 ml) were added to water and the reaction mixture was vigorously stirred at a temperature of 30° C. for 24 hours. The obtained product was extracted with ethyl acetate and the solvent was removed to give pure product.

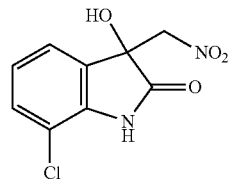

HRMS(ESI) for $C_9H_7N_2O_4ClNa$ $[M + Na]^+$ 264.91414.
YIELD 91%

Example 7

Wherein, R=H, $R_1$=Br

Preparation of 7-bromo-3-hydroxy-3-(nitromethyl)indolin-2-one 7-bromoisatin (0.113 g) and nitromethane (0.15 ml) were added to water and the reaction mixture was vigorously stirred at a temperature of 30° C. for 24 hours. The obtained product was extracted with ethyl acetate and purified by silica gel column chromatography using ethyl acetate/hexane as eluents to afford pure product.

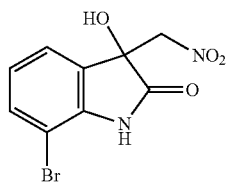

ESI MS(m/z): 308 $(M + Na)^+$
YIELD 86%

Example 8

Wherein, R=H, $R_1$=I

Preparation of 3-hydroxy-7-iodo-3-(nitromethyl)indolin-2-one 7-iodoisatin (0.136 g) and nitromethane (0.15 ml) were added to water and the reaction mixture was vigorously stirred at a temperature of 30° C. for 24 hours. The obtained product was extracted with ethyl acetate and purified by silica gel column chromatography using ethyl acetate/hexane as eluents to afford pure product.

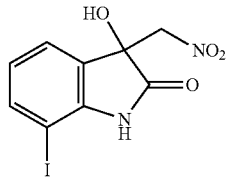

ESI MS(m/z): 356 $(M + Na)^+$.
YIELD 84%

Example 9

Wherein, R=H, $R_1$=F

Preparation of 7-fluoro-3-hydroxy-3-(nitromethyl)indolin-2-one 7-fluoroisatin (0.082 g) and nitromethane (0.15 ml) were added to water and the reaction mixture was vigorously stirred at a temperature of 30° C. for 24 hours. The obtained product was extracted with ethyl acetate and purified by silica gel column chromatography using ethyl acetate/hexane as eluents to afford pure product.

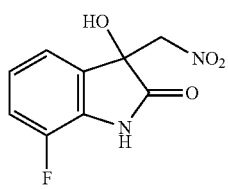

ESI MS(m/z): 249 (M + Na)+
YIELD 85%

Example 10

Wherein $R_1$=NO$_2$, R=H

Preparation of
3-hydroxy-5-nitro-3-(nitromethyl)indolin-2-one 5-nitroisatin (0.081 g) and nitromethane (0.15 ml) were added to water (2 ml) and the reaction mixture was vigorously stirred at a temperature of 30° C. for 12 hours. The product was extracted with ethyl acetate and recrystallized with MeOH to afford pure product.

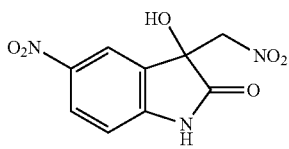

ESI MS(m/z): 276 (M + Na)+
YIELD 88%

Example 11

Wherein $R_1$=CH$_3$, R=H

Preparation of
3-hydroxy-5-methyl-3-(nitromethyl)indolin-2-one 5-methyl isatin (0.08 g) and nitromethane (0.15 ml) were added to water and the reaction mixture was vigorously stirred at a temperature of 50° C. for 24 hours. The product was extracted with ethyl acetate and purified by silica gel column chromatography using ethyl acetate/hexane as eluents to afford pure product.

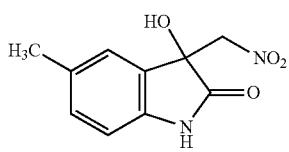

m.p 153° C., HRMS(ESI) for C$_{10}$H$_{10}$N$_2$O$_4$Na [M + Na]+ 245.0538.
YIELD 75%

Example 12

Wherein $R_1$=OCF$_3$, R=H

Preparation of 3-hydroxy-5-trifluoromethoxy-3-(nitromethyl)indolin-2-one 5-trifluoromethoxy isatin ((0.115 g) and nitromethane (0.1 ml) were added to water and the reaction mixture was vigorously stirred at a temperature of 30° C. for 20 minutes. The obtained product was extracted with ethyl acetate and the solvent was removed to give pure product.

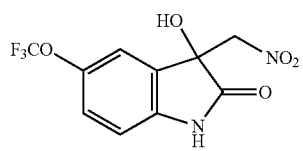

m.p 117° C., HRMS(ESI) for C$_{10}$H$_7$O$_5$N$_2$F$_3$Na [M + Na]+ 315.0199
YIELD 91%

Example 13

Wherein $R_1$=H, R=CH$_3$

Preparation of
3-hydroxy-1-methyl-3-(nitromethyl)indolin-2-one

N-methyl isatin (0.08 g) and nitromethane (0.15 ml) were added to water and the reaction mixture was vigorously stirred at a temperature of 30° C. for 24 hours. The obtained product was extracted with ethyl acetate and purified by silica gel column chromatography using ethyl acetate/hexane as eluents to afford pure product.

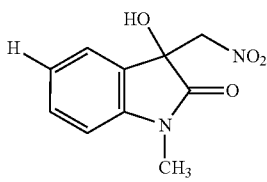

m.p 99° C., HRMS(ESI) for C$_{10}$H$_{11}$N$_2$O$_4$ [M + 1]+ 223.0718
YIELD 85%

Example 14

Wherein $R_1$=H, R=CH$_2$Ph

Preparation of
1-benzyl-3-hydroxy-3-(nitromethyl)indolin-2-one

N-benzyl isatin (0.118 g) and nitromethane (0.15 ml) were added to water and the reaction mixture was vigorously stirred at a temperature of 30° C. for 11 hours. The obtained product was extracted with ethyl acetate and the solvent was removed to give pure product.

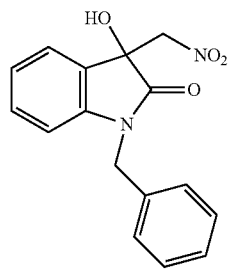

m.p 134° C., HRMS(ESI) for $C_{16}H_{15}N_2O_4$ [M + 1]$^+$ 299.1031
YIELD 92%

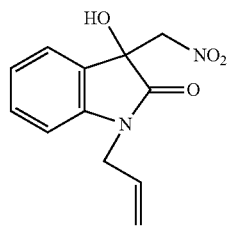

HRMS(ESI) for $C_{12}H_{13}N_2O_4$ [M + 1]$^+$ 249.0875
YIELD 75%

Example 17

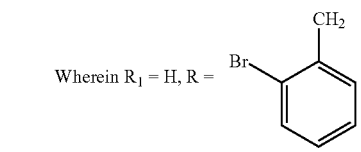

Wherein $R_1$ = H, R =

Example 15

Wherein $R_1$=Cl, R=$CH_2$Ph

Preparation of 1-benzyl-5-chloro-3-hydroxy-3-(nitromethyl)indolin-2-one 1-benzyl-5-chloroindoline-2,3-dione (0.135 g) and nitromethane (0.15 ml) were added to water and the reaction mixture was vigorously stirred at a temperature of 30° C. for 6 hours. The obtained product was extracted with ethyl acetate and purified by silica gel column chromatography using ethyl acetate/hexane as eluents to afford pure product.

Preparation of 1-(2-bromobenzyl)-3-hydroxy-3-(nitromethyl)indolin-2-one 1-(2-bromobenzyl)indoline-2,3-dione (0.158 g) and nitromethane (0.15 ml) were added to water and the reaction mixture was vigorously stirred at a temperature of 30° C. for 30 hours. The obtained product was extracted with ethyl acetate and purified by silica gel column chromatography using ethyl acetate/hexane as eluents to afford pure product.

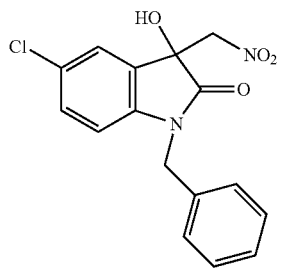

HRMS(ESI) for $C_{16}H_{14}N_2O_4$ [M + 1]$^+$ 333.06366.
YIELD 91%

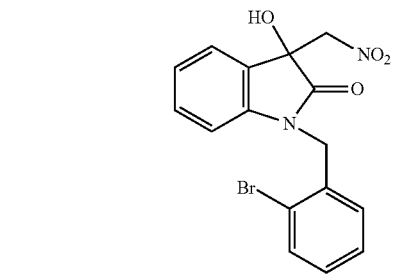

HRMS(ESI) for $C_{16}H_{13}O_4N_2BrNa$ [M + Na]$^+$ 398.99509
YIELD 85%

Example 18

Example 16

Wherein $R_1$=H, R=$C_3H_5$

Procedure for 1-allyl-3-hydroxy-3-(nitromethyl)indolin-2-one 1-allylindoline-2,3-dione (0.093 g) and nitromethane (0.15 ml) were added to water and the reaction mixture was vigorously stirred at a temperature of 40° C. for 24 hours. The obtained product was extracted with ethyl acetate and purified by silica gel column chromatography using ethyl acetate/hexane as eluents to afford pure product.

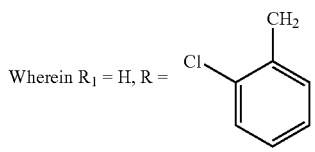

Wherein $R_1$ = H, R =

Preparation of 1-(2-chlorobenzyl)-3-hydroxy-3-(nitromethyl)indolin-2-one 1-(2-chlorobenzyl)indoline-2,3-dione (0.135 g) and nitromethane (0.15 ml) were added to water and the reaction mixture was vigorously stirred at a temperature of 30° C. for 9 hours. The obtained product was extracted with ethyl acetate and the solvent was removed to give pure product.

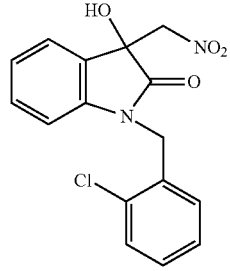

HRMS(ESI) for $C_{16}H_{14}N_2O_4Cl$ $[M+1]^+$ 333.06366.
YIELD 91%

Example 19

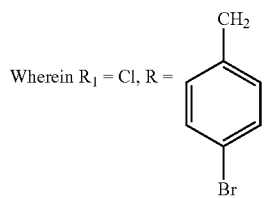

Wherein $R_1 = Cl$, $R =$

Preparation of 1-(4-bromobenzyl)-5-chloro-3-hydroxy-3-(nitromethyl)indolin-2-one 1-(4-bromobenzyl)-5-chloroindoline-2,3-dione (0.175 g) and nitromethane (0.15 ml) were added to water and the reaction mixture was vigorously stirred at a temperature of 30° C. for 24 hours. The obtained product was extracted with ethyl acetate and purified by silica gel column chromatography using ethyl acetate/hexane as eluents to afford pure product.

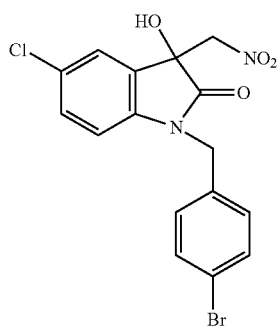

HRMS(ESI) for $C_{16}H_{13}N_2O_4BrCl$ $[M+1]^+$ 412.9624.
YIELD 83%

Example 20

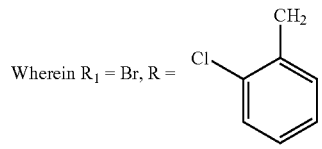

Wherein $R_1 = Br$, $R =$

Preparation of 5-bromo-1-(2-chlorobenzyl)-3-hydroxy-3-(nitromethyl)indolin-2-one 1-(2-chlorobenzyl)-5-bromoindoline-2,3-dione (0.175 g) and nitromethane (0.15 ml) were added to water and the reaction mixture was vigorously stirred at a temperature of 30° C. for 24 hours. The obtained product was extracted with ethyl acetate and purified by silica gel column chromatography using ethyl acetate/hexane as eluents to afford pure product.

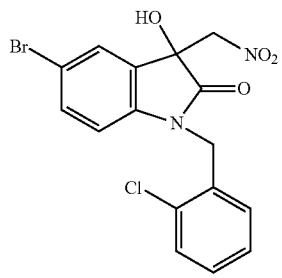

ESI MS(m/z): 413 $(M+1)^+$
YIELD 85%

Example 21

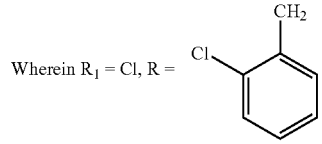

Wherein $R_1 = Cl$, $R =$

Preparation of 5-chloro-1-(2-chlorobenzyl)-3-hydroxy-3-(nitromethyl)indolin-2-one 1-(2-chlorobenzyl)-5-chloroindoline-2,3-dione (0.153 g) and nitromethane (0.15 ml) were added to water and the reaction mixture was vigorously stirred at a temperature of 30° C. for 18 hours. The formed solid product was filtered and recrystallized with MeOH to afford pure product.

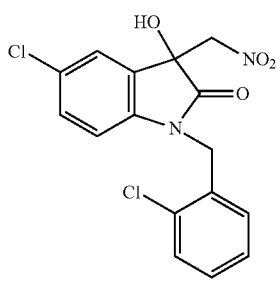

ESI MS(m/z): 389 (M + Na)⁺
YIELD 91%

ADVANTAGES OF THE PRESENT INVENTION

The main advantages and novelty of the present invention are:
1. Development of a simple, green method for the synthesis of some known 3-substituted-3-hydroxy-oxindole derivatives.
2. For the first time we have developed a simple process for the synthesis of novel 3-substituted-3-hydroxy-oxindole derivatives.
3. The process involves water as solvent, no base, room temperature, with excellent yields of the desired product serves as invincible system for the production of Henry adducts from isatin.
4. Compared to reported methods for Henry reactions of isatins, ours is a ecofriendly one involving water as a solvent.
5. Yet, another advantage of present process is that in many cases further purification of the reaction product is not required, which makes the process very simple and economical.
6. In a nutshell the process of the present invention is simple, cost-effective, non-hazardous and well suited for large-scale production.
7. The so obtained Henry adducts from our invention can serve as synthetic precursors for natural products like dioxibrassinin and spirobrassinin which exhibits various biological properties including antifungal and anticancer activities. Spirobrassinin displays antifungal, antitumor activities as well as oviposition stimulation.
8. 3-(Nitromethylene)indolin-2-one analogues, whose synthetic precursor is 3-hydroxy-3-nitromethyl-1,3-dihydro-indol-2-one exhibited potent cytotoxic activity against A549 and P388 lung cancer cell lines.

We claim:
1. A 3-hydroxy-3-nitromethyl indolin-2-one derivative compound of general formula II:

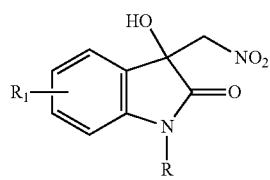

(II)

wherein:
R=H or C₇H₆—X;
R₁=H, X₁ at C-7 position, or X₂ at C-5 position;
X=H, Br, or Cl;
X₁=I or F;
X₂=H, Cl or Br,
wherein:
when, R=H; R₁=X₁ at C-7 position;
when, R=C₇H₆—X; then R₁=X₂ at C-5 position;
when X=H; then R₁=Cl at C-5 position;
when X=Cl; then R₁=X₂ at C-5 position;
when X=Br; then R₁=H or Cl at C-5 position;
and
further wherein when R₁=H, X is Br or Cl at ortho position; and wherein when R₁=Cl at C-5 position, X is Br at para position.

2. The compound as claimed in claim 1, wherein the 3-hydroxy-3-nitromethylindolin-2-one derivatives include:
3-hydroxy-7-iodo-3-(nitromethyl)indolin-2-one (represented by STR1);
7-fluoro-3-hydroxy-3-(nitromethyl)indolin-2-one (represented by STR2);
1-benzyl-5-chloro-3-hydroxy-3-(nitromethyl)indolin-2-one (represented by STR3);
1-(2-bromobenzyl)-3-hydroxy-3-(nitromethyl)indolin-2-one (represented by STR4);
1-(2-chlorobenzyl)-3-hydroxy-3-(nitromethyl)indolin-2-one (represented by STR5);
1-(4-bromobenzyl)-5-chloro-3-hydroxy-3-(nitromethyl)indolin-2-one (represented by STR6);
5-bromo-1-(2-chlorobenzyl)-3-hydroxy-3-(nitromethyl)indolin-2-one (represented by STR7); and
5-chloro-1-(2-chlorobenzyl)-3-hydroxy-3-(nitromethyl)indolin-2-one (represented by STR8).

3. The compound as claimed in claim 1, wherein the novel 3-hydroxy-3-nitromethylindolin-2-one derivatives have the structure:

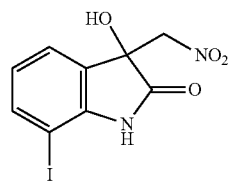

STR1

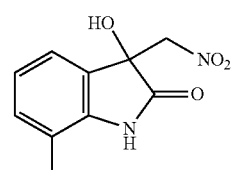

STR2

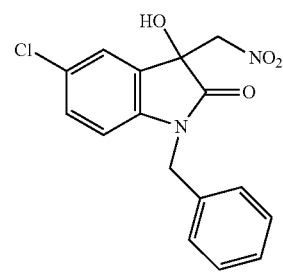

STR3

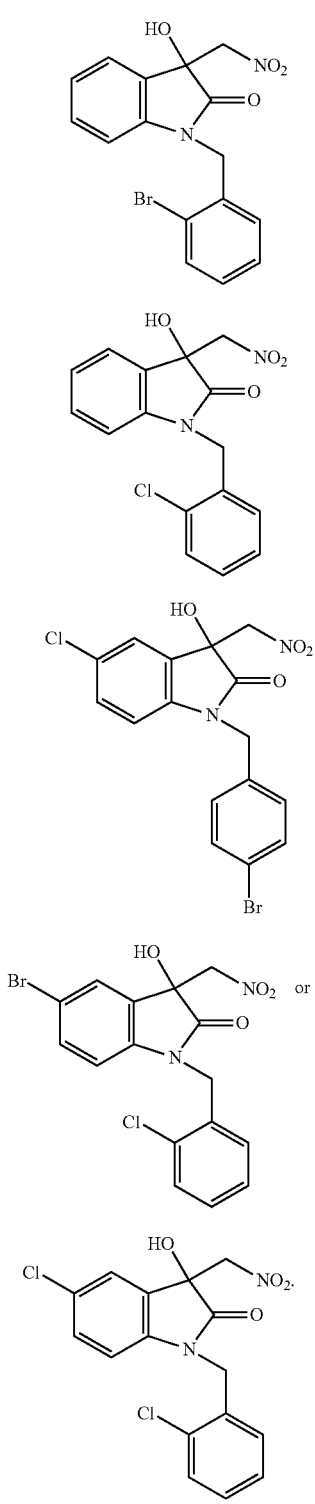

STR4

STR5

STR6

STR7

STR8

4. A compound as claimed in claim 1, wherein the compound is useful in synthesis of potent anticancer compounds.

5. A process for preparing 3-hydroxy-3-nitromethylindolin-2-ones of general formula (II) comprising the steps:
(a) reacting isatin or a substituted isatin of formula (I) with nitromethane in aqueous solvent as shown in the below equation at a temperature ranging between 30 to 50° C. for a period ranging between 10 min to 48 hrs; and wherein R and R1 in formula I and formula II are:
R=H; CH$_3$, C$_3$H$_5$, C$_7$H$_6$—X;
R$_1$=H, X$_1$ at C-7 position, or X$_2$ at C-5 position;
X=H, Br, or Cl;
X$_1$ =F, Cl, Br, or I; and
X$_2$=H, F, Cl, Br, I, NO$_2$, CH$_3$, OCF$_3$;
wherein:
when R=H, then R$_1$=X$_1$ at C-7 position, or X$_2$ at C-5 position;
when R=CH$_3$, C$_3$H$_5$, C$_7$H$_6$ —X; then R$_1$=H;
when, R=C$_7$H$_6$ —X; then R$_1$=X$_2$ at C-5 position;
when X=H, Cl, or Br; then R$_1$=Cl at C-5 position;
when X=Cl; then R$_1$=Br at C-5 position; and
(b) purifying the product by recrystallization or chromatographic methods.

6. The process as claimed in claim 5, wherein the ratio of isatin or substituted isatin and nitromethane is ranging between 1:3 to 1:5.

7. The process as claimed in claim 5, wherein the chromatographic method used is selected form a group consisting of column chromatograph, TLC.

8. The process as claimed in claim 5, wherein the recrystallisation is carried out using solvent selected from a group consisting of MeOH, EtOAc.

9. The process as claimed in claim 5, wherein the 3-hydroxy-3-nitromethylindolin-2-ones obtained by the process include:
3-hydroxy-3-(nitromethyl)indolin-2-one (represented by STR9);
5-chloro-3-hydroxy-3-(nitromethyl)indolin-2-one (represented by STR10);
5-bromo-3-hydroxy-3-(nitromethyl)indolin-2-one (represented by STR11);
3-hydroxy-5-iodo-3-(nitromethyl)indolin-2-one (represented by STR12);
5-fluoro-3-hydroxy-3-(nitromethyl)indolin-2-one (represented by STR13);
7-chloro-3-hydroxy-3-(nitromethyl)indolin-2-one (represented by STR14);
7-bromo-3-hydroxy-3-(nitromethyl)indolin-2-one (represented by STR15);
3-hydroxy-7-iodo-3-(nitromethyl)indolin-2-one (represented by STR1);
7-fluoro-3-hydroxy-3-(nitromethyl)indolin-2-one (represented by STR2);
3-hydroxy-5-nitro-3-(nitromethyl)indolin-2-one (represented by STR16);
3-hydroxy-5-methyl-3-(nitromethyl)indolin-2-one (represented by STR 17);

3-hydroxy-5-trifluoromethoxy-3-(nitromethyl)indolin-2-one (represented by STR18);
3-hydroxy-1-methyl-3-(nitromethyl)indolin-2-one (represented by STR19);
1-benzyl-3-hydroxy-3-(nitromethyl)indolin-2-one (represented by STR20);
1-benzyl-5-chloro-3-hydroxy-3-(nitromethyl)indolin-2-one (represented by STR3);
1-allyl-3-hydroxy-3-(nitromethyl)indolin-2-one (represented by STR21);
1-(2-bromobenzyl)-3-hydroxy-3-(nitromethyl)indolin-2-one (represented by STR4);
1-(2-chlorobenzyl)-3-hydroxy-3-(nitromethyl)indolin-2-one (represented by STR5);
1-(4-bromobenzyl)-5-chloro-3-hydroxy-3-(nitromethyl)indolin-2-one (represented by STR6);
5-bromo-1-(2-chlorobenzyl)-3-hydroxy-3-(nitromethyl)indolin-2-one (represented by STR7); and
5-chloro-1-(2-chlorobenzyl)-3-hydroxy-3-(nitromethyl)indolin-2-one (represented by STR8).

10. The process as claimed in claim 5, wherein the 3-hydroxy-3-nitromethylindolin-2-ones obtained by the process have the structure:

STR9
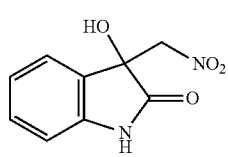

STR10
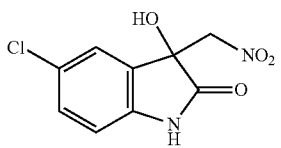

STR11
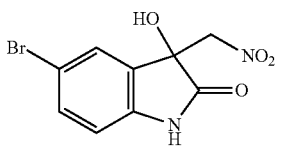

STR12
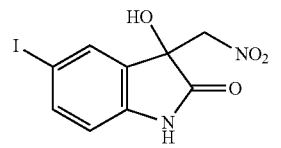

STR13
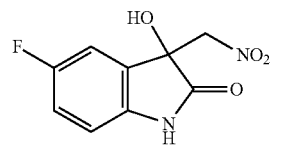

STR14
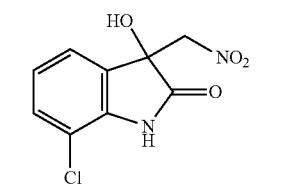

STR15
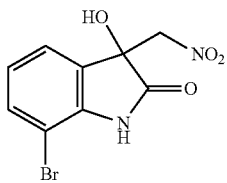

STR1
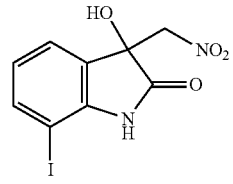

STR2
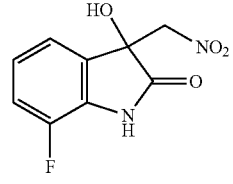

STR16
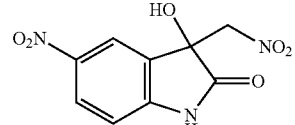

STR17
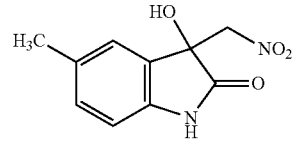

STR18

STR19
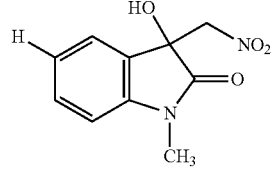

STR20
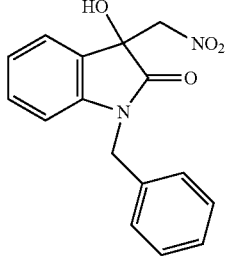

27
-continued
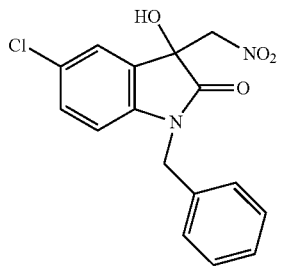
STR3
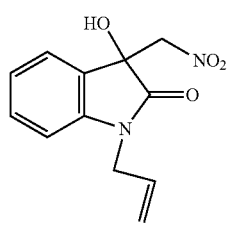
STR20
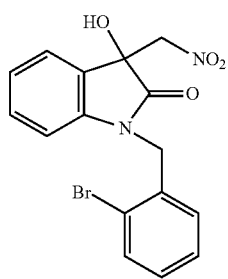
STR4
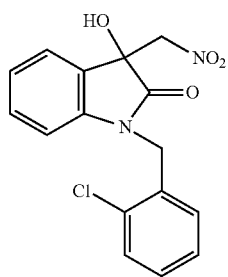
STR5
28
-continued
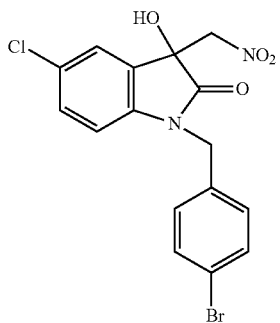
STR6
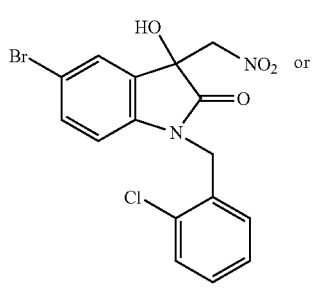
STR7
or
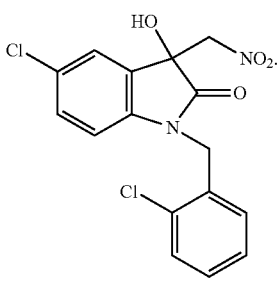
STR8
* * * * *